United States Patent

Macher et al.

[11] Patent Number: 4,698,331
[45] Date of Patent: Oct. 6, 1987

[54] 2,3-DIAMINO-2,3-DIDESOXYHEXOSE DERIVATIVES AND THEIR USE

[75] Inventors: Ingolf Macher; Frank M. Unger, both of Vienna, Austria

[73] Assignee: Sandoz Ltd., Basel, Switzerland

[21] Appl. No.: 815,097

[22] PCT Filed: Apr. 17, 1985

[86] PCT No.: PCT/EP85/00171
§ 371 Date: Dec. 18, 1985
§ 102(e) Date: Dec. 18, 1985

[87] PCT Pub. No.: WO85/04881
PCT Pub. Date: Nov. 7, 1985

[30] Foreign Application Priority Data
Apr. 21, 1984 [DE] Fed. Rep. of Germany ....... 3415102
Apr. 21, 1984 [DE] Fed. Rep. of Germany ....... 3415100

[51] Int. Cl.$^4$ .......................... A61K 31/70; C07H 5/06
[52] U.S. Cl. ......................................... 514/25; 514/23; 536/17.2; 536/17.9; 536/18.7
[58] Field of Search ................... 536/18.7, 17.2, 17.9; 514/23, 25

[56] References Cited

U.S. PATENT DOCUMENTS 4,384,998   5/1983   Durette ................................ 536/4.1
4,481,196  11/1984   Teraji et al. ......................... 536/17.2

*Primary Examiner*—Johnnie R. Brown
*Assistant Examiner*—Elli Peselev

*Attorney, Agent, or Firm*—Gerald D. Sharkin; Robert S. Honor; Thomas O. McGovern

[57] ABSTRACT

Compounds of formula I

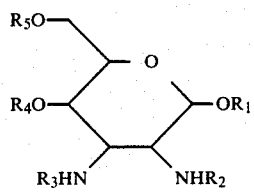

wherein
$R_2$ and $R_3$ are the same or different and each represent unsubstituted or substituted acyl, and (a) $R_1$ represents lower alkyl, aralkyl or the phosphate, pyrophosphate, phosphorylethanolamine or pyrophosphorylethanolamine group, $R_4$ represents the phosphate, pyrophosphate, phosphorylethanolamine or pyrophosphorylethanolamine group and one of $R_1$ and $R_4$ may additionally represent hydrogen and $R_5$ represents hydrogen or a glycosyl radical or (b) $R_1$ represents hydrogen, lower alkyl or aralkyl and $R_4$ and $R_5$ represent hydrogen, which compounds are indicated for use as pharmaceuticals, in particular as immunostimulants.

9 Claims, No Drawings

2,3-DIAMINO-2,3-DIDESOXYHEXOSE DERIVATIVES AND THEIR USE

The present invention concerns 2,3-diamino-2,3-didesoxyhexose derivatives, processes for their preparation, pharmaceutical compositions containing them and their use as pharmaceuticals especially as immunostimulants.

More particularly the invention concerns compounds of formula I

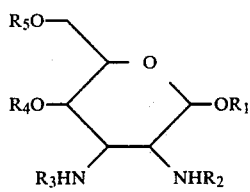

wherein
$R_2$ and $R_3$ are the same or different and each represent unsubstituted or substituted acyl,
and
(a) $R_1$ represents lower alkyl, aralkyl or the phosphate, pyrophosphate, phosphorylethanolamine or pyrophosphorylethanolamine group, $R_4$ represents the phosphate, pyrophosphate, phosphorylethanolamine or pyrophosphorylethanolamine group and one of $R_1$ and $R_4$ may additionally represent hydrogen and $R_5$ represents hydrogen or a glycosyl radical
or
(b) $R_1$ represents hydrogen, lower alkyl or aralkyl and $R_4$ and $R_5$ represent hydrogen.

The compounds of formula I may be obtained according to the invention by (a), to prepare compounds of formula Ia,

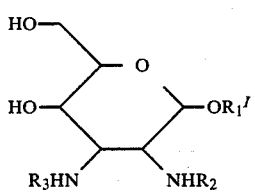

acylating the corresponding compound of formula II

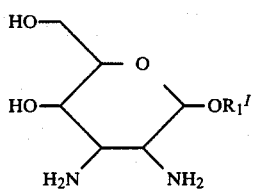

whereby
$R_2$ and $R_3$ are the same and are as defined above and
$R_1{}^I$ stands for hydrogen, lower alkyl or aralkyl,
(b), to prepare a compound of formula Ia wherein $R_2$ and $R_3$ are different acylating a compound of formula IIa,

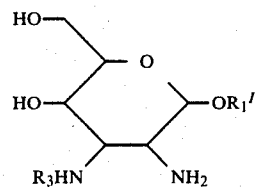

wherein
$R_1{}^I$ and $R_3$ are as defined above or
(c), to prepare a compound of formula Ib,

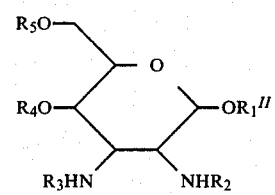

wherein
$R_2$ to $R_5$ are as defined above and
$R_1{}^{II}$ represents hydrogen, lower alkyl, aralkyl or the phosphate, pyrophosphate, phosphorylethanolamine or pyrophosphorylethanolamine group whereby $R_1{}^{II}$ and $R_4$ are not simultaneously hydrogen, reacting a compound of formula Ic,

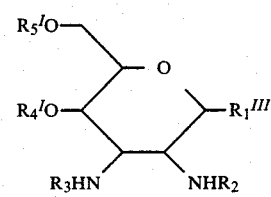

wherein
$R_2$ and $R_3$ are as defined for formula I,
$R_1{}^{III}$ represents hydrogen, lower alkyl, aralkyl or a protecting group and
$R_4{}^I$ represents hydrogen or a protecting group whereby $R_1{}^{III}$ and $R_4{}^I$ are not simultaneously protecting groups, and $R_5{}^I$ represents a protecting group or a glycosyl radical with a corresponding phosphorous compound
and if required removing any protecting groups present in the compounds obtained.

Processes (a) and (b) can be carried out for example by dissolving the compound of formula II or IIa together with the acylating agent in a solvent inert under the reaction conditions e.g. in a di-(lower)alkylcarboxylic acid amide such as dimethylformamide and allowing them to react at room temperature.

Process (c) can be carried out for example by dissolving a compound of formula Ic in a solvent inert under the reaction conditions e.g. in a cyclic ether such as tetrahydrofuran reacting same at low temperature e.g. $-70°$ with butyllithium in an aliphatic hydrocarbon e.g. in hexane and then adding phosphorochloridate. The free OH groups of the phosphate radical may also be protected e.g. by benzyl and these protecting groups can be removed after reaction e.g. hydrogenolytically.

Other protecting groups may also be removed in conventional manner. Thus, for example, protecting groups as $R_1^{III}$ or $R_4^I$ are usually removed acidically e.g. with an aqueous acid (ion exchanger).

End products can be isolated and purified in conventional manner.

The compounds of formula II are also new and form part of the invention. They can be prepared e.g. according to the following reaction scheme

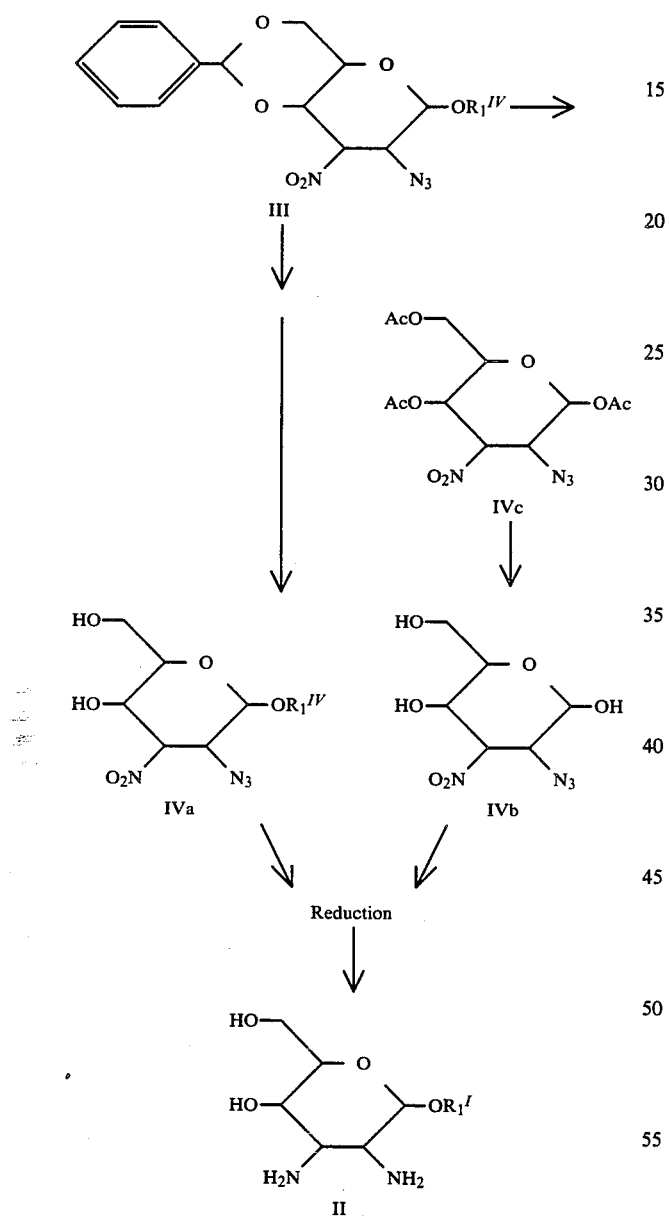

$R_1^{IV}$=lower alkyl or aralkyl, Ac=acetyl. The compounds of formulae IVa and IVb may be directly reduced to compounds of formula II.

By controlling the reaction conditions (e.g. time, quantity of catalyst) it is possible, to prepare the compounds of formula IIa, by in a first step reducing only the azido group. Following protection of the resulting amino group the nitro group can be reduced. In this manner starting materials of formula IIa may be obtained from which end-products wherein $R_2$ and $R_3$ are different may be prepared.

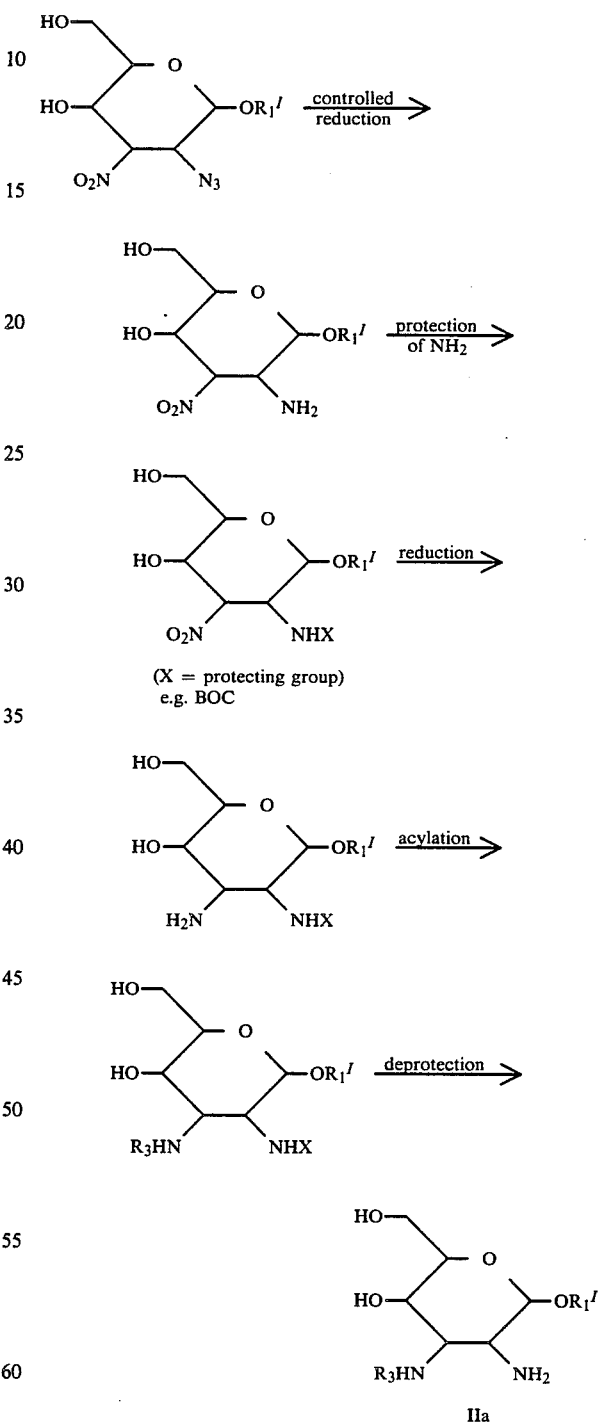

The compounds of formula Ic can be prepared from compounds of formula Ia or Ib wherein $R_2$ and $R_3$ are the same or different e.g. according to the following reaction scheme

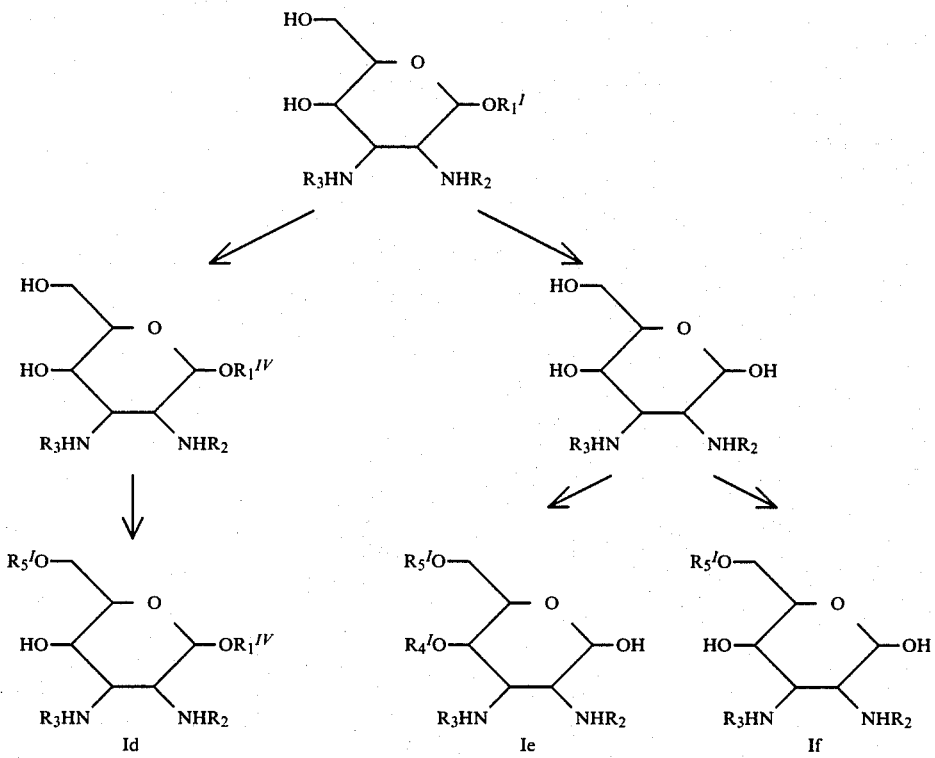

The compounds, Id, Ie, If may be protected as appropriate in conventional manner.

The remaining starting materials are either known or may be prepared analogously to known compounds.

$R_2$ and $R_3$ are the same or different preferably the same and represent an acyl group such as an alkylcarbonyl group having for example 4 to 20 preferably 12 to 16 and particularly 14 carbon atoms which may be substituted e.g. in the 3-position by OH, acetoxy or an acyloxy whereby acyl is as defined herein. The C-3 atom is preferably in R-configuration.

As stated compounds of formula I wherein the 3-position of the acyl especially alkylcarbonyl side chain is substituted can exist in the form of R- and S-antipodes or as a racemic mixture thereof. The individual antipodes can be obtained e.g. by using acylating agents themselves in isomeric form. Compounds of the formula I may also be in the form of the α- and β-anomers with respect to the hexose ring or mixtures thereof. The invention covers the individual isomeric forms and mixtures thereof.

Compounds of formula I wherein at least one of $R_1$ and $R_4$ represents a phosphate, pyrophosphate, phosphorylethanolamine or pyrophosphorylethanolamine radical are preferred; particularly preferred are compounds of formula I wherein at least one of $R_1$ and $R_4$ is a phosphate radical.

A preferred individual compound is 2,3-diamino-2,3-didesoxy-2,3-di-N-[3(R)-hydroxytetradecanoyl]-α-D-glucopyranosyl-phosphate.

Compounds wherein at least one of $R_1$ and $R_4$ represents a phosphorus bearing group with free hydroxy may be in free form or in the form of salts or esters. Free forms may be converted into salt or ester forms in conventional manner. The compounds capable of forming salts and esters may also be recovered after the preparation in free form or in salt or ester form. Examples of suitable salts are such as in the examples.

In accordance with the present invention it has been found that the compounds of formula I are useful as pharmaceutical agents, in particular as immunostimulants.

The immunostimulant activity of the subject compounds may be shown in standard tests both in vitro and in vivo demonstrating lymphocyte and/or macrophage proliferation effects. Thus positive immunostimulant activity is shown for compounds of the invention e.g. in the following test methods:

1. BACTERIAL SEPTICEMIA IN THE NEUTROPENIC MOUSE

This model permits testing of substance-linked increase in resistance in bacterially infected, neutropenic mice. To induce neutropenia 20 female $B_6D_2F_1$-mice receive subcutaneously, on day zero 1×200 mg/kg body weight of cyclophosphamide dissolved in 0.2 ml aqua. dest. The test substance, dissolved if possible in physiological saline or if not possible dissolved otherwise (0.3 ml), is administered parenterally (primarily i.p.) or also orally at day three. Infection follows on day 4 by i.v. administration of the inoculum in question in a volume of 0.2 ml (cell count/mouse e.g. *Pseud.aeruginosa* Δ12; 1×10⁵, *E.coli* Δ120; 2×10⁶). The test animals are observed up to 10 days following infection and the deaths/day registered. The following parameters were evaluated in comparison with infection controls and standards.

(a) average survival period
(b) survival rate.

The compounds of formula I showed marked improvements in both parameters compared with untreated infection controls in both experimental Pseudomonas and *E.coli* infection on parenteral administration.

2. IN VITRO DETERMINATION OF INCREASED KILLING OF BACTERIA BY POLYMORPHONUCLEAR LEUKOCYTES

This test serves to detect substances which increase the intrinsic microbicidal activity of neutrophils. The source of neutrophils is peritoneal exudate of mice pretreated for 4 hours with 5% casein, thioglycolate or 0.1% glycogen. Test substances are dissolved as far as possible in Hanks balanced salt solution. Water-insoluble substances are dissolved in a small quantity of dimethyl sulfoxide and diluted to the required volume with Hanks solution. The incubation mixture containing test substance, neutrophils and bacteria opsonised in 10% homologous serum is shaken for 2 hours at 37° whereupon the surviving bacteria are determined as cell counts. The differences in killing of test cells by leukocytes in the presence or absence of test substances is evaluated using a t-test. Opsonised bacteria in the presence of test substance absent neutrophils serve as further control.

3. KILLING OF BACTERIA BY NEUTROPHILS OBTAINED FROM MICE PRETREATED WITH TEST SUBSTANCE

The test illustrates in vitro the increased capacity for killing bacteria of neutrophils from animals pretreated with test substance. Groups of 4 mice each are treated either s.c. or i.p. with test substance. 24 hours later the peritoneal neutrophils are washed-out after pretreatment with 5% casein, thioglycolate or 0.1% glycogen. The incubation mixtures containing neutrophils from treated (or control) animals as well as bacteria opsonised with 10% homologous serum are shaken for 2 hours at 37° whereupon the surviving bacteria are determined as cell counts. The killing of bacteria by leukocytes from control and substance treated animals is compared using a t-test.

4. DETERMINATION OF ENDOTOXIN ACTIVITY OF TEST SUBSTANCES IN LIMULUSAMEBOCYTE LYSATE TEST

Endotoxin catalyses the activation of a proenzyme in the gelling of limulusamebocytelysate. The separation of p-nitroaniline from a colour-forming substrate is measured. The degree of separation is determined by photometry whereby the correlation between absorption and endotoxin conc. (or -activity by analogs) is linear in the range of 0.01 to 0.1 ug/ml (comparison with absorption values of a standard endotoxin). A series dilution of 1:10 is prepared from each sample (dissolved in pyrogen-free aqua bidestillata sterilis) and each series run with a control sample. 100 µl sample or standard or control are treated with 100 ul limulusamebocyte lysate and the reaction stopped at 10 minutes with 200 ul 50% acetic acid. After shaking of the samples the absorption is measured against the control value (dist. $H_2O$) in a spectral photometer at 405 nm. The establishment of the endotoxin content (endotoxin activity) of the sample as endotoxin units (E.U.) is carried out by calculation of a linear regression using the values of the standard endotoxin.

5. ENDOTOXIN SHOCK INDUCTION IN THE MOUSE

This test illustrates the induction of an endotoxin shock or a clinically similar condition with lethal outcome by LPS-like substances in galactosamine-(GalN)-sensitised mice. Male C 57 bl. mice (6 animals per group) receive simultaneously i.p. 8 mg of GalN dissolved in 0.5 ml PBS and 0.1 µg LPS from *salmonella abortus equi* (Sigma), dissolved in 0.2 ml physiological saline. This treatment leads to death of all animals within 5–9 hours (C. Galanos, et.al., Proc. Natl. Acad. Sci., USA, 76(1979) 59395943). In place of the LPS in the standard procedure test substances are administered at various dosages parenterally or orally either simultaneously with the GalN or one or more times prior to or following GalN treatment. The evaluation of the result is carried out by comparing the lowest dose which leads to the death of all animals in a group or by calculation of an $LD_{50}$ by the Spearman-Kärber method.

6. INDUCTION OF LPS (ENTOTOXIN)-TOLERANCE

The daily parenteral administration of LPS to mice can induce a so-called tolerance which protects the animals against the lethal effects of LPS following GalN administration. (cf. test 5). Using compounds of formula I for three days at an i.p. dosage of 0.25 mg/day/mouse it was possible to induce a tolerance such that all animals survived a lethal dose of LPS (0.1 µg/mouse) administered 3 days after final treatment with test substance.

The compound of formula I are accordingly useful as immuno-stimulants, e.g. as immunological adjuvants, as systemic immuno-potentiators and as stimulators of non-specific host resistance. Compounds of the invention are thus suitable for e.g. the treatment or supportive treatment (i.e. in combination with other specific or supportive therapy) of conditions associated with impared immune response, especially impared humoral response and/or delayed-type hypersensitivity and of conditions where elevation of the immune response is otherwise indicated. In particular, the compounds of the invention are useful for the treatment or supportive treatment of morbid conditions arising from idiopathic immune deficiencies or as occurring in geriatirc patients and patients with severe burns or general infections. The compounds of the invention are also indicated for the treatment or supportive treatment of viral illnesses (such as disseminated herpes, progressive vaccinia and disseminated varicella) as well as of Hodgkins Disease and other malignant tumors.

In addition the compounds of formula I are suitable for the prophylaxis of endotoxin shock e.g. as caused by accidents, burns and surgical operations.

For the above uses the dosage will, of course, vary depending upon the compound employed, the mode of administration and therapy desired. However, in general, satisfactory results are obtained when administered at a dosage of from about 10 µg/kg to 10 mg/kg once for adjuvant effect, e.g. in supportive treatment, or daily. For daily administration the compound is conveniently given in divided doses 2 to 4 times a day or in sustained release form. For the larger mammals the total single or daily dosage is in the range of from about 0.1 mg to about 70 mg and dosage forms suitable for oral administration comprise from about 0.025 mg to about 35 mg or, in the case of single dosages, up to 70 mg of active ingredient admixed with a solid or liquid pharmaceutical carrier.

Having regard to their utility as immuno-stimulants, compounds of the invention are also useful as adjuvants for vaccines. For such use satisfactory results are obtained at a dose of from about 0.01 mg to about 1.0 mg/kg on the day of vaccination, with an optical follow-up application at the same dosage 2 to 4 weeks later. For larger mammals a suitable dosage form for oral administration as a vaccine adjuvant comprises from about 0.5 mg to about 100 mg or, preferably, about 70 mg active ingredient.

As already noted, a suitable daily dosage for any particular compound of the invention will depend, inter al., on its relative potency of activity. A suitable dose for the preferred compound in accordance with the invention, namely 2,3-diamino-2,3-didesoxy-2,3-di-N-[3(R)-hydroxytetradecanoyl]-α-D-glucopyranosyl-phosphate would be 12,5 mg/kg.

The compounds of formula I, wherein $R_1$ and/or $R_4$ represent a phosphorus containing group with free hydroxy may be used in free form or in the form of pharmaceutically acceptable salts or esters, which exhibit the same order of activity as the free forms.

The compounds may be administered enterally e.g. orally or parenterally e.g. as injectables.

Pharmaceutical compositions comprising the compounds of the invention may be prepared in accordance with standard galenical techniques, e.g. by admixture with conventional pharmaceutically acceptable diluents, carriers or other excipients. Such formulations are conveniently compounded, e.g. in tablet or capsule form or in forms suitable for injection.

In accordance with the foregoing the present invention also provides a compound of the invention as hereinbefore defined for use as a pharmaceutical, in particular for use as an immunostimulant, especially for use in treatment or supportive treatment, e.g. of conditions associated with impared immune response as hereinbefore set forth or as a prophylactic against endotoxin shock.

In a further aspect the invention also provides a method of stimulating the immune response of a subject in need of such treatment which method comprises administering an effective amount of a compound of the invention as hereinbefore defined.

In a yet further aspect the invention also provides a pharmaceutical composition comprising a compound of the invention as hereinbefore defined, together with a pharmaceutically acceptable diluent or carrier therefor.

The following examples illustrate the invention whereby temperatures are in degrees centigrade.

EXAMPLE 1

2,3Diamino-2,3-didesoxy-2,3-di-N-[3(R)-tetradecanoyloxytetradecanoyl]-α-D-glucopyranosyl-phosphate (Process c)

(a)

2,3-Diamino-2,3-didesoxy-2,3-di-N-[3(R)-tetradecanoyloxytetradecanoyl]-4,6-O-isopropylidene-α-D-glucopyranosyl-dibenzylphosphate To a solution of 30 mg of 2,3-diamino-2,3-didesoxy-2,3-di-N-[3(R)-tetradecanoyloxytetradecanoyl]-4,6-O-isopropylidene-D-glucose in 10 ml of tetrahydrofuran cooled to −70° are added 20 μl of 1.6 m butyllithium in hexane and the mixture stirred for 2 minutes. A solution of dibenzylphosphorochloridate obtained from 755 mg of dibenzylphosphite and 365 mg of N-chlorosuccinimide in 5 ml of benzene is then added. The mixture is slowly allowed to rise to room temperature, one drop of acetic acid added and the mixture concentrated under vacuum. The residue is chromatographed twice over silica gel (chloroform/methanol=98/2; toluene/ethylacetate=1/1) to obtain the title compound Rf (chloroform/methanol=95/5): 0.72.

$^1$H-NMR (CDCl$_3$); 7.37 (s, 10H, phenyl); 6.44[d, $J_{2,NH}$=8 Hz, 1H, NH—C(2)]; 6.03[d, $J_{3,NH}$=8, 1 Hz, NH—C(3)]; 5.71 [dd, $J_{1,2}$=3 Hz, $J_{1,P}$=6 Hz, 1H, H—C(1)]; 5.08 (m, 6H, 2x-CH$_2$-phenyl, 2x—cH—O—CO—); 4.25 [ddd, $J_{2,3}$=11 Hz, $J_{3,4}$=10 Hz, 1H, H—C(3)]; 4.03 [m, 1H, H—C(2)]; 3.79 [m, 1H, H—C(5)]; 3.70 (m, 2H, H—C(6)]; 3.54 (t, $J_{4,5}$=9.5 Hz, 1H, H—C(4)].

(b)

2,3-Diamino-2,3-didesoxy-2,3-di-N-[3(R)-tetradecanoyloxytetradecanoyl]-α-D-glucopyranosyl-phosphate (deprotection)

10 mg of-2,3-Diamino-2,3-didesoxy-2,3-di-N-[3(R)-tetradecanoyloxytetradecanoyl]-4,6-O-isopropylidene-α-D-glucopyranosyl-dibenzylphosphate are dissolved in 5 ml of tetrahydrofuran and hydrogenated at normal pressure (10% Pd/C 5 mg). On completion of the hydrogenation (ca. 30 minutes) the catalyst is filtered off and 2.5 ml of water and a strongly acid ion-exchanger added to the filtrate. The mixture is heated for ca. 2 hours at 45°. The ion-exchanger is then filtered off and the product converted into the corresponding salt for m e.g. into the Na-salt with Amberlite AG 50W-X8, Na$^+$, into the triethylamine salt with 0.01N aq. triethylamine solution or into the tris-hydroxymethylaminomethane salt with a 0.01N solution of tris-hydroxymethylaminomethane.

Rf (n-butanol/pyridine/acetic acid/water=50/20/6/24): 0.65.

$^1$H—NMR (CDCl$_3$/CD$_3$OD=3/1): 0.88 (t, J=6,5 Hz, 12H, —CH$_3$); 1.27 (m, 76H, —CH$_2$—); 1.60 (m, 8H, CO—C—CH$_2$—); 2.31 (t, J=6,5 Hz, 4H, CO—CH$_2$—); 2.44 (m, 4H, CO—CH$_2$—CO); 3.20 to 4.20 [m, H—C(2) to H—C(6)]; 5.20 (m, 2H, CO—O—CH—); 5.55 [dd, $J_{1,P}$=6,2 Hz, $J_{1,2}$=3,0 Hz, 1H, H—C(1)].

EXAMPLE 2

2,3-Diamino-2,3-didesoxy-2,3-di-N-[3(R)-hydroxytetradecanoyl]-α-D-glucopyranosyl-phosphate (Process c)

(a)

2,3-Diamino-2,3-didesoxy-2,3-di-N-[3(R)-benzyloxytetradecanoyl]-4,6-O-isopropylidene-α-D-glucopyranosyl-dibenzylphosphate Analogous to Example 1(a). Twice chromatographed over silica gel (chloroform/methanol=98/2; toluene/ethylacetate=10/7).

Rf (toluene/ethylacetate=5/4): 0.38; $[\alpha]_D^{20}$=+40,2° (c=1,1 in chloroform (b)

2,3-Diamino-2,3-didesoxy-2,3-di-N-[2(R)-hydroxytetradecanoyl]-α-D-glucopyranosyl-phosphate (deprotection)

Analogous to Example 1(b).
Rf (chloroform/methanol/glacial acetic acid/water=125/75/10/20): 0.45.

EXAMPLE 3

2,3-Diamino-2,3-didesoxy-2,3-di-N-[3(R)-acetoxytetradecanoyl]-α-D-glucopyranosyl-phosphate (Process c)

(a) 2,3-Diamino-2,3-didesoxy-2,3-di-N-[3(R)-acetoxytetradecanoyl]-4,6-O-isopropylidene-α-D-glucopyranosyl-dibenzylphosphate Analogous to Example 1(a).
$[\alpha]_D^{25} = 30.1°$ (c=1 in chloroform.

(b)
2,3-Diamino-2,3-didesoxy-2,3-di-N-[3(R)-acetoxytetradecanoyl]-α-D-glucopyranosyl-phosphate (deprotection)

Analogous to Example 1(b).
Rf (butanol/pyridine/glacial acetic acid/water=50/20/6/24): 0.55.
$[\alpha]_D^{20} = +37.9°$ (c=0.5 in chloroform/methanol=1/1).

EXAMPLE 4

Methyl 2,3-diamino-2,3-didesoxy-2,3-di-N-[3(R)-tetradecanoyloxytetradecanoyl]-4-O-phosphoryl-β-D-glucopyranoside (Process c)

(a) Methyl 2,3-diamino-4-O-dibenzylphosphoryl-2,3-didesoxy-2,3-di-N-∂3(R)tetradecanoyloxytetradecanoyl]-6-O-tert.butyldimethylsilyl-β-D-glucopyranoside To a −20° solution of 640 mg of methyl 2,3-diamino-2,3-didesoxy-2,3-di-N-[3(R)-tetradecanoyloxytetradecanoyl]-6-O-tert.butylidimethylsilyl-β-D-glucopyranoside in 30 ml of dry tetrahydrofuran are added 0.375 ml of 1.6 m butyllithium in hexane and ca. 2 minutes later 180 mg of dibenzylphosphorochloridate in benzene. The mixture is allowed to rise to room temperature, then cooled to −20° and the mixture neutralised with acetic acid. The solution is concentrated by evaporation and the residue chromatographed over silica gel (toluene/ethylacetate=4/1).
Rf (toluene/ethylacetate=3/1): 0.55; $[\alpha]_D^{20} = 29.7°$ (c=1 in chloroform).

(b) Methyl 2,3-diamino-2,3-didesoxy-2,3-di-N-[3(R)-tetradecanoyloxytetradecanoyl]-4-O-phosphoryl-β-D-glucopyranoside (deprotection)

A solution of 400 mg methyl 2,3-diamino-4-O-dibenzylphosphoryl-2,3-didesoxy-2,3-di-N-[3(R)-tetradecanoyloxytetradecanoyl]-6-O-tert.butyldimethylsilyl-β-D-glucopyranoside in 100 ml of tetrahydrofuran is hydrogenated for 1 hour at normal pressure with 100 mg 10% Pd/C. The mixture is treated with 10 ml of water, filtered and the filtrate heated to 50° for 10 minutes with Amberlite AG 50W-X8H+. It is then filtered and most of the tetrahydrofuran evaporated off. The aqueous suspension is lyophilised; a minor protion without neutralization and the main portion following neutralisation with triethylamine.
Rf (butanol/pyridine/glacial acetic acid/water=50/20/6/24): 0.75.
$[\alpha]_D^{20} = -103.6°$ (c=1 in chloroform/methanol=1/1).

The acidic lyophilisate is dissolved in chloroform/methanol (1/1) and treated with etheric diazomethane solution. After concentration by evaporation the dimethylester of the title compound is obtained.

EXAMPLE 5

Methyl 2,3-diamino-2,3-didesoxy-2,3-di-N-[3(R)-hydroxytetradecanoyl]-4-O-phosphoryl-β-D-glucopyranoside (Process c)

Analogous to Example 4.

(a) Methyl 2,3-diamino-4-O-dibenzylphosphoryl-2,3-didesoxy-2,3-di-N-[3(R)-benzyloxytetradecanoyl]-6-O-tert.butyldimethylsilyl-β-D-glucopyranoside
Rf (chloroform/methanol=95/5)=0.41.

(b) Methyl 2,3-diamino-2,3-didesoxy-2,3-di-N-[3(R)-hydroxytetradecanoyl]-4-O-phosphoryl-β-D-glucopyranoside (deprotection)
Rf (butanol/pyridine/glacial acetic acid/water=50/20/6/24)=0.55.
$[\alpha]_D^{20} = -56°$ (c=0.5 in chloroform/methanol=1/1).

EXAMPLE 6

2,3-Diamino-2,3-didesoxy-3-N-[3(R)-hydroxytetradecanoyl]-2-N-[3(R)-tetradecanoyloxytetradecanoyl]-α-D-glucopyranosyl-phosphate (Process c)

(a) 2,3-Diamino-2,3-didesoxy-3-N-[3(R)-benzyloxytetradecanoyl]-2-N-[3(R)-tetradecanoyloxytetradecanoyl]-4,6-O-isopropylidene-α-D-glucopyranosyl-dibenzylphosphate A solution of 308 mg of 2,3-diamino-2,3-didesoxy-3-N-[3(R)-benzyloxytetradecanoyl]-2-[3(R)-tetradecanoyloxytetradecanoyl]-4,6-O-isopropylidene-D-glucopyranose in 20 ml of abs. tetrahydrofuran is cooled to −70° 0.6 ml of a 1.6 m solution of butyllithium in hexane added dropwise and after ca. 5 minutes a solution of 95 mg of dibenzylphosphorochloridate in benzene added. The solution is stirred for 30 min. at −20°, allowed to rise to room temperature, chilled again and neutralised with acetic acid.

The solution is concentrated by evaporation and the residue chromatographed over silica gel (toluene/ethylacetate=2/1)
Rf (toluene/ethylacetate=1/1)=0.7.
$[\alpha]_D^{20} = +23.3°$ (c=1.2 in chloroform).

(b) 2,3-Diamino-2,3-didesoxy-3-N-[3(R)-hydroxytetradecanoyl]-2-N-[3(R)-tetradecanoyloxytetradecanoyl]-α-D-glucopyranosylphosphate (deprotection)

160 mg of 2,3-Diamino-2,3-didesoxy-3-N-[3(R)-benzyloxytetradecanoyl]-2-N-[3(R)-tetradecanoyloxytetradecanoyl]-4,6-O-isopropylidene-α-glucopyranosyldibenzyl-phosphate are dissolved in 30 ml of tetrahydrofuran, palladium on charcoal (30 mg, 10% Pd) added and the mixture hydrogenated under normal pressure for several of hours. The catalyst is then filtered off, 6 ml of water and Amberlite AG50W-X8H+ added and the mixture stirred for ca. 5 hours at 40°–50°. The ionexchanger is removed and a small amount of the solution treated with etheric diazomethane until pale yellow, concentrated by evaporation and the residue submitted to NMR spectroscopy. The main portion of the solution is neutralised with 0.01N triethylamine solution and then lyophilised. The title compound is thus obtained as bistriethylamine salt.

Rf (chloroform/methanol/water/acetic acid=25/15/4/2): 0.58.

EXAMPLE 7

2,3-Diamino-2,3-didesoxy-2,3-di-N-[3(R)-tetradecanoyloxytetradecanoyl]-D-glucose (Process a)

A solution of 28 mg of 2,3-diamino-2,3-didesoxy-D-glucose and 120 mg of N-[3(R)-tetradecanoyloxytetradecanoyloxy]succinimide is taken to pH 8 with diisopropylethylamine and stirred for 48 hours at room temperature. The solvent is then removed and the residue chromatographed over silica gel (chlorform/methanol=95/5). The title compound is obtained as an anomeric mixture ($\alpha/\beta=3/1$).

Rf (chloroform/methanol=9/1): 0.23.
$[\alpha]_D^{20} = -2.1°$ (c=1 chloroform/methanol=1/1).

EXAMPLE 8

2,3-Diamino-2,3-didesoxy-2,3-di-N-[3(R)-hydroxytetradecanoyl]-D-glucose (Process a)

A solution of 50 mg of 2,3-diamino-2,3-didesoxy-D-glucose and 136 mg of N-[3(R)-hydroxytetradecanoyloxy]succinimide in 15 ml of dimethylformamide is taken to pH 8 with diisopropylethylamine and stirred for 15 hours at room temperature. The reaction mixture is poured into water and the precipitate filtered off, washed with 2×10 ml methanol and 2×10 ml chloroform and dried to obtain the title compound: m.p. 200° (decomp.).

EXAMPLE 9

2,3-Diamino-2,3-didesoxy-2,3-di-N-[3(R)-acetoxytetradecanoyl]-D-glucose (Process a)

Analogous to Example 8.
Rf (chloroform/methanol=9/1)=0.25.

EXAMPLE 10

Methyl 2,3-diamino-2,3-didesoxy-2,3-di-N-[3(R)-hydroxytetradecanoyl]-$\beta$-D-glucopyranoside (Process a)

A solution of 96 mg of methyl 2,3-diamino-2,3-didesoxy-$\beta$-D-glucopyranoside and 341 mg of N-[3(R)-hydroxytetradecanoyloxy]succinimide in 15 ml of dimethylformamide is stirred for 24 hours at room temperature. The reaction mixture is then poured into 300 ml of water the precipitate filtered off and washed with 3×15 ml warm methanol (40°-50°) to give the amorphous title compound.

Rf (chloroform/methanol=8/2)=0.53.
$^1$H—NMR (DMSO-d$_6$): 0.87 (t, J=6.5 Hz, 6H, 2×—CH$_3$); 1.25 (m, 40H, —CH$_2$—); 2.12 and 2.15 (each 1d, J=6.5 Hz, each 2H, —CO—CH$_2$—); 3.35 (s, 3H, —OCH$_3$); 3.0 to 3.9 (m); 4.35 (m, 3H, 2×O—CH—, —OH); 4.70 [d, J$_{1,2}$=5 Hz, 1H, H—C(1)]; 7.6 (m, 2H, NH).

EXAMPLE 11

Methyl 2,3-diamino-2,3-didesoxy-2,3-di-N-[3(R)-tetradecanoyloxytetradecanoyl]-$\beta$-D-glucopyranoside (Process a)

23 mg of Methyl 2,3-diamino-2,3-didesoxy-$\beta$-D-glucopyranoside and 130 mg of N-[3(R)-tetradecanoyloxytetradecanoyloxy]siuccinimide are dissolved in 10 ml of dimethylformamide and stirred for 48 hours at room temperature. The suspension is concentrated by evaporation and the residue chromatographed over silica gel (chloroform/methanol=95/5).

Rf (chloroform/methanol=95/5); 0.42.
$[\alpha]_D^{20} = -22.0°$ (c=1 in chloroform).

EXAMPLE 12

Methyl 2,3-diamino-2,3-didesoxy-2,3-di-N-[3(R,S)-tetradecanoyloxytetradecanoyl]-$\beta$-D-glucopyranoside (Process a)

490 mg of Methyl 2,3-diamino-2,3-didesoxy-$\beta$-D-glucopyranoside and 2.8 g of N-[3(R,S)-tetradecanoyloxytetradecanoyloxy]succinimide are dissolved in dimethylformamide and stirred for 24 hours at room temperature. The suspension is concentrated by evaporation and the residue chromatographed over silica gel to give the title compound as a mixture of the 4 possible diastereomers.

Rf (chloroform/methanol=95/5)=0.42.
$[\alpha]_D^{25} = -18.2°$ (c=1 in chloroform).

EXAMPLE 13

2,3-Diamino-2,3-didesoxy-2,3-di-N-[3(R)-hydroxytetradecanoyl]-4-O-phosphoryl-$\alpha$-D-glucopyranosyl-phosphate (Process c)

(a)

2,3-Diamino-2,3-didesoxy-4-O-dibenzylphosphoryl-2,3-di-N-[3(R)-benzyloxytetradecanoyl]-6-O-trityl-$\alpha$-D-glucopyranosyl-dibenzylphosphate 105 mg of 2,3-Diamino-2,3-didesoxy-2,3-di-N-[3(R)-benzyloxytetradecanoyl]-6-O-trityl-D-glucopyranose are phosphorylated analogously to Example 6 at room temperature with 0.4 mmol of butyllithium and 0.3 mmol dibenzylphosphorochloridate. Chromatographic purification on silica gel (toluene/ethyl acetate=7/3) yields the title compound.

Rf (toluene/ethylacetate=7/3): 0.22.

(b)

2,3-Diamino-2,3-didesoxy-2,3-di-N-[3(R)-hydroxytetradecanoyl]-4-O-phosphoryl-$\alpha$-D-glucopyranosyl-phosphate 80 mg of 2,3-Diamino-2,3-didesoxy-4-O-dibenzylphosphoryl-2,3-di-N-[3(R)-benzyloxytetradecanoyl]-6-O-trityl-$\alpha$-D-glucopyranosyl-dibenzylphosphate are dissolved in 20 ml of tetrahydrofuran and hydrogenated with 20 mg of 10% palladium on charcoal. The catalyst is filtered off, the filtrate treated with 5 ml of water and warmed with Amberlite AG50W-X8H$^+$. After filtration and substantial removal of tetrahydrofuran the remaining suspension is further diluted with water and neutralised with 0.01N triethylamine solution. Insolubles are removed and the solution lyophilised.

Rf (chloroform/methanol/glacial acetic acid/water=125/75/10/20): 0.35.

The required starting materials may be prepared as follows.

(A)
2,3-Diamino-2,3-didesoxy-2,3-di-N-[3(R)-tetradecanoyloxytetradecanoyl]-4,6-O-isopropylidene-D-glucose (for Example 1)

To a solution of 34 mg of 2,3-diamino-2,3-didesoxy-2,3-di-N-[3(R)-tetradecanoyloxytetradecanoyl]-D-glucose in 15 ml of dimethylformamide are added 4 mg of 2-propenylmethylether and a catalytic amount of p-toluenesulfonic acid and the reaction mixture stirred at room temperature. After 2 hours a further 4 mg of 2-propenylmethylether are added and stirring continued for 4 hours. The mixture is concentrated by evaporation and the residue chromatographed over silica gel (chloroform/methanol=95/5) to obtain the title compound.
Rf (chloroform/methanol=95/5): 0.51.

(B)
2,3-Diamino-2,3-didesoxy-2,3-di-N-[3(R)-acetoxytetradecanoyl]-4,6-O-isopropylidene-D-glucose (for Example 3)

Analogous to (A).
Rf (chloroform/methanol=9/1): 0.47.
$[\alpha]_D^{25} = -9.9°$ (c=1 in chloroform/methanol=1/1).

(C) Methyl
2,3-diamino-2,3-didesoxy-2,3-di-N-[3(R)-tetradecanoyloxytetradecanoyl]-6-O-tert.butyldimethylsilyl-β-D-glucopyranoside (for Example 4)

A mixture of 1.12 g of methyl 2,3-diamino-2,3-didesoxy-2,3-di-N-[3(R)-tetradecanoyloxytetradecanoyl]-β-D-glucopyranoside, 226 mg of tert.butyldimethylsilylchloride and 205 mg of imidazole in 20 ml of dimethylformamide is stirred for 1.5 hours at room temperature. Excess reagent is destroyed with water, the solvent removed by evaporation and the residue chromatographed (toluene/ethylacetate=3/1).
Rf (toluene/ethylacetate=2/1): 0.63.
$[\alpha]_D^{20} = 15.4°$ (c=0.74 in chloroform).

(D) Methyl
2,3-diamino-2,3-didesoxy-2,3-di-N-[3(R)-benzyloxytetradecanoyl]-6-O-tert.butyldimethylsilyl-β-D-glucopyranoside (for Example 5)

Analogous to (C).
Chromatographic purification on silica gel with chloroform/methanol (95/5) gives the title compound.
Rf (chloroform/methanol=95/5): 0.37.

(E)
2,3-Diamino-2,3-didesoxy-3-N-[3(R)-benzyloxytetradecanoyl]-2-N-[3(R)-tetradecanoyloxytetradecanoyl]-4,6-O-isopropylidene-D-glucopyranose (for Example 6)

(a)
2-Amino-2,3-didesoxy-3-nitro-2-N-tert.butyloxycarbonyl-D-glucopyranose

A solution of 2.5 g of 2-azido-2,3-didesoxy-3-nitro-D-glucopyranose in 80 ml of 1N HCl is stirred for 2 hours under hydrogen at normal pressure with 500 mg of 10% palladium on charcoal.
The catalyst is then filtered off, the solution concentrated by evaporation and the residue taken up in water and lyophilised. The lyophilisate is dissolved in 50 ml of dimethylformamide, 1.5 g of triethylamine and 2.34 g of di-tert.butyldicarbonate added and the mixture stirred for 5 hours at room temperature. Triethylamine hydrochloride is filtered off the filtrate concentrated by evaporation and the residue chromatographed (chloroform/methanol=9/1).
Rf (chloroform/methanol=9/1): 0.18.

(b)
2,3-Diamino-2,3-didesoxy-3-N-[3(R)-benzyloxytetradecanoyl]-2-N-tert.butyloxycarbonyl-D-glucopyranose 1.31 g of 2-Amino-2,3-didesoxy-3-nitro-2-N-tert.butyloxycarbonyl-D-glucopyranose are dissolved in 200 ml of methanol and hydrogenated for 4 hours at normal pressure with ca. 500 mg of freshly prepared Raney-Nickel. The catalyst is then filtered off, the filtrate concentrated by evaporation and the residue dried under high vacuum. The residue is dissolved in 30 ml of dry dimethylformamide, N-[3(R)-benzyloxytetradecanoyloxy]succinimide added and the solution left for 2 days at room temperature. Usual working up and chromatographic purification (chloroform/methanol=95/5) yields the title compound as a mixture of both anomers.
Rf (Chloroform/Methanol=95/5): 0.3 and 0.25.

(c)
2,3-Diamino-2,3-didesoxy-3-N-[3(R)-benzyloxytetradecanoyl-2-N-[3(R)-tetradecanoyloxytetradecanoyl]-D-glucopyranose To a suspension of 520 mg of 2,3-diamino-2,3-didesoxy-3-N-[3(R)-benzyloxytetradecanoyl]-2-N-tert.butyloxycarbonyl-D-glucopyranose in 20 ml of dichloromethane are added 2 ml of trifluoracetic acid. After 3 hours at room temperature a clear solution results which is concentrated by evaporation and dried under high vacuum. The residue is dissolved in 20 ml of dimethylformamide, 470 mg of N-[3(R)-tetradecanoyloxytetradecanoyloxy]succinimide added and the pH adjusted to 8 with diisopropyl ethylamine. Reaction is complete after 2 days at 40°. The solvent is evaporated off and the residue chromatographed (chloroform/methanol=9/1).
Rf (chloroform/methanol=9/1): 0.43.
$[\alpha]_D^{20} = 0°$ (c=2 in chloroform).

(d)
2,3-Diamino-2,3-didesoxy-3-N-[3(R)-benzyloxytetradecanoyl]-2-N-[3(R)-tetradecanoyloxytetradecanoyl]-4,6-O-isopropylidene-D-glucopyranose 412 mg of 2,3-Diamino-2,3-didesoxy-3-N-[3(R)-benzyloxytetradecanoyl]-2-N-[3(R)-tetradecanoyloxytetradecanoyl]-D-glucopyranose are suspended in dry dimethylformamide, a catalytic amount, of p-toluene sulfonic acid and 43 mg of isopropenylmethylether added and the reaction mixture stirred at room temperature. After 2 hours everything is dissolved and the reaction is terminated by addition of solid NaHCO₃. The solvent is evaporated off and the residue chromatographed (chloroform/methanol=95/5).
Rf (chloroform/methanol=95/5): 0.27.
$[\alpha]_D^{20} = 0°$ (c=1 in chloroform).

(F) 2,3-Diamino-2,3-didesoxy-D-glucose (for Examples 7 to 9)

(a) 2-Azido-2,3-didesoxy-3-nitro-1,4,6-tri-O-acetyl-α-D-glucopyranose

A solution of 6 g of methyl-2-azido-4,6-O-benzylidene-2,3-didesoxy-3-nitro-β-D-glucopyranoside in a mixture of 24 ml of acetic acid, 24 ml of aceticanhydride and 16 ml of sulfuric acid is allowed to stand for 15 hours at room temperature, 200 ml of sodium acetate/acetic acid buffer then added and the mixture poured into 2 l of 5% ice-cold sodium acetate solution whereupon a part of the product precipitates. The precipitate is filtered off and dissolved in chloroform. The aqueous phase is saturated with NaCl and extracted with chloroform. The chloroform solution is combined with the extract, washed with saturated NaCl solution, dried ($Na_2SO_4$) and the solvent evaporated off on a Rotavapor. The title compound is obtained after crystallisation from ethanol.

m.p. 118°–120°.
$[\alpha]_D^{25} = 129$ (c=1 in chloroform).
Rf (ethanol/petrolether=7/3): 0.50.

(b) 2-Azido-2,3-didesoxy-3-nitro-D-glucose 2.6 g of 2-Azido-2,3-didesoxy-3-nitro-1,4,6-tri-O-acetyl-α-D-glucopyranose are refluxed with 130 ml 6N HCl until all has dissolved (ca. 5 minutes). The solution is concentrated under high vacuum, the residue dissolved in water, lyophilised and the lyophilisate dried over KOH in an exsiccator.

Rf (chloroform/methanol=8/2): 0.62.

(c) 2,3-Diamino-2,3-didesoxy-D-glucose 300 mg of 2-Azido-2,3-didesoxy-3-nitro-D-glucose are hydrogenated under normal pressure for 1 hour in 60 ml of 0.5N HCl (10% Pd/C, 40 mg). After filtration and 2 lyophilisations the title compound is obtained as dihydrochloride.

m.p. 180°–185° (decomp.).
$[\alpha]_D^{23} = 52.5°$ (c=1.05 in water).

(G) 2,3-Diamino-2,3-didesoxy-2,3-di-N-[3(R)-benzyloxytetradecanoyl]-6-O-trityl-D-glucopyranose (for Example 13)

To a solution of 1.96 g of 2,3-diamino-2,3-didesoxy-2,3-di-N-[3(R)-benzyloxytetradecanoyl]-D-glucopyranose in 100 ml of pyridine and maintained at room temperature are added in portions over 2 days ca. 4 g of tritylchloride. When no starting material more is present the excess tritylchloride is hydrolysed and the solution evaporated to dryness. The residue is triturated with 100 ml of toluene/ethylacetate 8/2, insoluble matter filtered off and the filtrate applied to a silica gel column and eluted with the same eluant. The amorphous title product is obtained as a mixture of anomers.

Rf (toluene/ethylacetate=7/3): 0.53 and 0.45.
$[\alpha]_D^{20} = +20°$ (c=1 in chloroform).

(H) 2,3-Diamino-2,3-didesoxy-2,3-di-N-[3(R)-benzyloxytetradecanoyl]-4,6-O-isopropylidene-D-glucopyranose (for Example 2)

(a) 2,3-Diamino-2,3-didesoxy-2,3-di-N-[3(R)-benzyloxytetradecanoyl]-D-glucopyranose Analogous to Example 7. Chromatographic purification with chloroform/methanol 9/1 as eluant yields the title compound as a mixture of anomers.

Rf (chloroform/methanol=9/1): 0.44 and 0.40.

(b) 2,3-Diamino-2,3-didesoxy-2,3-di-N-[3(R)-benzyloxytetradecanoyl]-4,6-O-isopropylidene-D-glucopyranose 1.66 g of 2,3-Diamino-2,3-didesoxy-2,3-di-N-[3(R)-benzyloxytetradecanoyl]-D-glycopyranose are suspended in 100 ml dimethylformamide, a catalytic amount of p-toluenesulfonic acid and 300 mg of isopropenylmethylether added and the mixture vigorously stirred for 3 hours. It is then neutralised with $NaHCO_3$ and the dimethylformamide distilled off. The residue is triturated with dichloromethane, insolubles filtered off and the solution evaporated to dryness. The residue is the chromatographically pure title compound obtained as a mixture of anomers.

Rf (chloroform/methanol=9/1): 0.68.
$[\alpha]_D^{20} = -1.1°$ (c=1 in chloroform/methanol=1/1).

(I) N-[3(R,S)-Tetradecanoyloxytetradecanoyloxy]succinimide

To a solution of 5.6 g of N-[3(R,S)-hydroxytetradecanoyloxy]succinimide in 150 ml pyridine cooled to 0° are added 4.9 g of tetradecanoylchloride and the reaction mixture maintained at 4° for 12 hours. Excess reagent is destroyed with water, the mixture concentrated by evaporation and the residue chromatographed over silica gel (toluene/ethylacetate=95/5) to obtained the title compound as a syrup.

Rf (toluene/ethylacetate=8/2): 0.76.
$^1H$—NMR ($CDCl_3$): 0.88 (t, J=6.5 Hz, 6H, —$CH_3$); 1.27 (m, 38H, —$CH_2$—); 1.70 (m, 4H, CO—C—$CH_2$— and O—C—$CH_2$—); 2.34 (t, J=7.0 Hz, 2H, CO—$CH_2$); 2.83 (s, 4H, CO—$CH_2$—$CH_2$—CO); 2.88 (d, J=6.5 Hz, 2H, CO—$CH_2$—C—O); 5.30 (qi, J=6.5 Hz, 1H, CO—O—CH—).

(J) N-[3(R)-Tetradecanoyloxytetradecanoyloxy]succinimide

Analogous to (I) to obtain crystalline title product.
m.p. 44°–45°.
$[\alpha]_D^{25} = +2.2°$ (c=1 in chloroform).

(K) N-[3(R)-Acetoxytetradecanoyloxy]succinimide 340 mg of N-[3(R)-Hydroxytetradecanoyloxy]succinimide are dissolved in a mixture of 40 ml of pyridine and 20 ml of aceticanhydride and maintained at 4° for 15 hours. The reaction mixture is concentrated under vacuum and reevaporated twice with toluene. The chromatographically pure title compound is obtained.

$^1H$—NMR ($CDCl_3$): 0.88 (t, J=6.5 Hz, 3H, —$CH_3$); 1.27 (m, 18H, —$CH_2$—); 1.70 (m, 2H, CO—C—$CH_2$—); 2.09 (s, 3H, CO—$CH_3$); 2.85 (s, 4H, CO—$CH_2$—CH-

2—CO); 2.88 (d, J=6.5 Hz, 2H, CO—CH$_2$—C—O); 5.30 (qi, J=6.5 Hz, 1H, CO—O—CH—).

We claim:

1. A compound of formula I

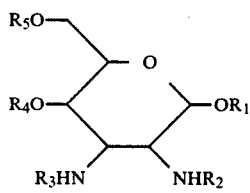

wherein

R$_2$ and R$_3$ are the same or different and each represent a C$_{4-20}$ alkylcarbonyl group or a C$_{4-20}$ alkylcarbonyl group substituted by OH, acetoxy or a C$_{4-20}$ alkylcarbonyloxy group, and (a) R$_1$ represents halogen, lower alkyl, aralkyl or the phosphate, pyrophosphate, phosphorylethanolamine or or pyrophosphorylethanolamine group, R$_4$ represents hydrogen, the phosphate, pryophosphate, phosphorylethanolamine or pyrophosphorylethanolamine group and R$_5$ represents hydrogen or a glycosyl radical, provided at least one of R$_1$ and R$_4$ is other than hydrogen, or (b) R$_1$ represents hydrogen, lower alkyl or aralkyl and R$_4$ and R$_5$ represent hydrogen in free form or, when at least one of R$_1$ and R$_4$ represents a phosphorus bearing group with a hydroxy, in the form of salts or esters.

2. A compound according to claim 1 wherein R$_2$ and R$_3$ are the same and represent a C$_{12-16}$alkylcarbonyl group or a C$_{12-16}$ alkylcarbonyl group substituted in the 3 position by OH, acetoxy or a C$_{12-16}$alkylcarbonyloxy group.

3. A compound according to claim 2 wherein said C$_{12-16}$ alkylcarbonyl group substituted in the 3 position is in R configuration.

4. A compound according to claim 1 wherein at least one of R$_1$ and R$_4$ is a phosphate radical.

5. A compound according to claim 1 selected from:
   (a) 2,3-Diamino-2,3-didesoxy-2,3-di-N-[3(R)-tetradecanoyloxytetradecanoyl]-α-D-glucopyranosyl-phosphate;
   (b) 2,3-Diamino-2,3-didesoxy-2,3-di-N-[3(R)-hydroxytetradecanoyl]-α-D-glucopyranosyl-phosphate;
   (c) 2,3-Diamino-2,3-didesoxy-2,3-di-N-[3(R)-acetoxytetradecanoyl]-α-D-glucopyranosyl-phosphate;
   (d) 2,3-Diamino-2,3-didesoxy-2,3-di-N-[3(R)-tetradecanoyloxytetradecanoyl]-D-glucose;
   (e) 2,3-Diamino-2,3-didesoxy-2,3-di-N-[3(R)-hydroxytetradecanoyl]-D-glucose;
   (f) 2,3-Diamino-2,3-didesoxy-2,3-di-N-[3(R)-acetoxytetradecanoyl]-D-glucose;
   (g) Methyl 2,3-diamino-2,3-didesoxy-2,3-di-N-[3(R)-hydroxytetradecanoyl]-β-D-glucopyranoside;
   (h) Methyl 2,3-diamino-2,3-didesoxy-2,3-di-N-[3(R)-tetradecanoyloxytetradecanoyl]-β-D-glucopyranoside; and
   (i) Methyl 2,3-diamino-2,3-didesoxy-2,3-di-N-[3(R,S)-tetradecanoyloxytetradecanoyl]-β-D-glucopyranoside.

6. A compound according to claim 1 selected from:
   (a) Methyl 2,3-diamino-2,3-didesoxy-2,3-di-N-[3(R)-tetradecanoyloxytetradecanoyl]-4-O-phosphoryl-β-D-glucopyranoside;
   (b) Methyl 2,3-diamino-2,3-didesoxy-2,3-di-N-[3(R)-hydroxytetradecanoyl]-4-O-phosphoryl-β-D-glucopyranoside;
   (c) 2,3-Diamino-2,3-didesoxy-3-N-[3(R)-hydroxytetradecanoyl]-2-N-[3(R)-tetradecanoyloxytetradecanoyl]-α-D-glucopyranosylphosphate; and
   (d) 2,3-Diamino-2,3-didesoxy-2,3-di-N-[3(R)-hydroxytetradecanoyl]-4-O-phosphoryl-α-D-glucopyranosylphosphate.

7. A method of inducing immunostimulation which comprises administering an immunostimulant effective amount of a compound of formula I according to claim 1 in free form or in the form of a pharmaceutically acceptable salt or ester.

8. A compound of formula II

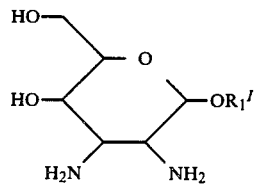

where R$_1^I$ is hydrogen, lower alkyl or aralkyl.

9. A pharmaceutical composition useful as an immunostimulant containing an immunostimulant effective amount of a compound of formula I according to claim 1 in free form or in the form of a pharmaceutically acceptable salt or ester and a pharmaceutically acceptable diluent or carrier therefor.

* * * * *